US008940493B2

(12) United States Patent
Gualberto et al.

(10) Patent No.: US 8,940,493 B2
(45) Date of Patent: Jan. 27, 2015

(54) CIRCULATING TUMOR CELL ASSAY

(75) Inventors: Antonio Gualberto, East Greenwich, RI (US); Maria Luisa Paccagnella, Noank, CT (US); Carrie L. Melvin, Ledyard, CT (US); Madeline I. Repollet, Fort Washington, PA (US); David Chianese, Ardmore, PA (US); Mark Carle Connelly, Doylestown, PA (US); Leonardus Wendelinus Mathias Marie Terstappen, Huntingdon Valley, PA (US)

(73) Assignees: Veridex LLC, New York, NY (US); Pfizer Inc., New York, NY (US)

( * ) Notice: Subject to any disclaimer, the term of this patent is extended or adjusted under 35 U.S.C. 154(b) by 982 days.

(21) Appl. No.: 12/303,243

(22) PCT Filed: May 29, 2007

(86) PCT No.: PCT/IB2007/001483
§ 371 (c)(1),
(2), (4) Date: Jul. 29, 2009

(87) PCT Pub. No.: WO2007/141626
PCT Pub. Date: Dec. 13, 2007

(65) Prior Publication Data
US 2010/0028915 A1     Feb. 4, 2010

Related U.S. Application Data (60) Provisional application No. 60/810,811, filed on Jun. 2, 2006.

(51) Int. Cl.
| | | |
|---|---|---|
| G01N 33/574 | (2006.01) | |
| G01N 33/50 | (2006.01) | |
| G01N 30/02 | (2006.01) | |

(52) U.S. Cl.
CPC ........ *G01N 33/5064* (2013.01); *G01N 33/5023* (2013.01); *G01N 33/574* (2013.01); *G01N 30/02* (2013.01); *G01N 2333/4745* (2013.01); *G01N 2800/52* (2013.01)
USPC .............................. 435/7.23; 436/64; 436/501

(58) Field of Classification Search
None
See application file for complete search history.

(56) References Cited

U.S. PATENT DOCUMENTS

| | | | |
|---|---|---|---|
| 4,551,435 A | 11/1985 | Liberti et al. | |
| 4,795,698 A | 1/1989 | Owen et al. | |
| 4,925,788 A | 5/1990 | Liberti | |
| 5,108,933 A | 4/1992 | Liberti et al. | |
| 5,200,084 A | 4/1993 | Liberti et al. | |
| 5,962,237 A | 10/1999 | Ts'o et al. | |
| 6,365,362 B1 | 4/2002 | Terstappen et al. | |
| 6,645,731 B2 | 11/2003 | Terstappen et al. | |
| 6,670,142 B2* | 12/2003 | Lau et al. ........................ | 506/10 |
| 2002/0098535 A1 | 7/2002 | Wang et al. | |
| 2002/0172987 A1 | 11/2002 | Terstappen et al. | |
| 2004/0157271 A1 | 8/2004 | Kirakossian et al. | |
| 2004/0229294 A1* | 11/2004 | Chan-Hui et al. ............. | 435/7.2 |
| 2005/0181463 A1 | 8/2005 | Rao et al. | |
| 2006/0045881 A1* | 3/2006 | Molldrem .................. | 424/178.1 |
| 2007/0037173 A1 | 2/2007 | Allard et al. | |
| 2009/0162853 A1* | 6/2009 | Clark et al. ...................... | 435/6 |

FOREIGN PATENT DOCUMENTS

| | | |
|---|---|---|
| CN | 1753686 | 3/2006 |
| JP | 2001-041959 A | 2/2001 |
| JP | 2002-503814 A | 2/2002 |
| JP | 2002-529704 A | 9/2002 |
| JP | 2004-534210 A | 11/2004 |
| JP | 2005-516217 A | 6/2005 |
| WO | WO 99/41613 | 8/1999 |
| WO | WO 00/26666 | 5/2000 |
| WO | WO 00/47998 | 8/2000 |
| WO | WO 01/12236 | 2/2001 |
| WO | WO 02/077604 | 10/2002 |
| WO | WO 03/018757 A2 | 3/2003 |
| WO | WO 03/065042 | 8/2003 |
| WO | WO 03/065042 A1 | 8/2003 |
| WO | WO 2005/016967 A2 | 2/2005 |
| WO | WO 2006/008639 A1 | 1/2006 |
| WO | WO 2006/041453 A1 | 4/2006 |
| WO | WO 2006/104474 A2 | 10/2006 |
| WO | WO 2007/141626 A1 | 12/2007 |

OTHER PUBLICATIONS

Mitsiades et al (Blood, vol. 100, abstract No. 637).*
Hofmann et al (Drug Discovery Today, Aug. 2005, vol. 10, pp. 1041-1046).*
Arteaga, C. L., et al., "Blockade of the Type I Somatomedin Receptor Inhibits Growth of Human Breast Cancer Cells in Athymic Mice," *Journal of Clinical Investigation*, 1989, 1418-1423, vol. 84.

(Continued)

*Primary Examiner* — Karen Canella
(74) *Attorney, Agent, or Firm* — Ropes & Gray LLP (57) ABSTRACT

Methods for the detection, enumeration and analysis of circulating tumor cells expressing insulin-like growth factor-1 receptors (IGF-1R) are disclosed. These methods are useful for cancer screening and staging, development of treatment regimens, and for monitoring for treatment responses, cancer recurrence or the like. Test kits that facilitate the detection, enumeration and analysis of such circulating tumor cells are also provided.

2 Claims, 9 Drawing Sheets

(56) References Cited

OTHER PUBLICATIONS

Attard, G., et al., "Phase I Trial Involving the Pharmacodynamic (PD) Study of Circulating Tumour Cells, of CP-751,871 (c), a Monoclonal Antibody Against the Insulin-Like Growth Factor 1 Receptor (IGF-1R), with Docetaxel (D) in Patients (p) with Advanced Cancer," *Journal of Clinical Oncology, Asco Annual Meeting Proceedings*, 2006, 3023, vol. 24, No. 18S.

Beitsch, P. D., et al., "Detection of Carcinoma Cells in the Blood of Breast Cancer Patients", *The American Journal of Surgery*, 2000, 446-449, vol. 180.

Berois, N., et al., "Detection of Rare Human Breast Cancer Cells. Comparison of an Immunomagnetic Separation Method with Immunocytochemistry and RT-PCR," *Anticancer Research*, 1997, 2639-2646, vol. 17.

Bubley, G. J., et al., "Eligibility and Response Guidelines for Phase II Clinical Trials in Androgen-Independent Prostate Cancer: Recommendations From the Prostate-Specific Antigen Working Group," *Journal of Clinical Oncology*, 1999, 3461-3467, vol. 17, No. 11.

Chadha, M., et al., "Predictors of Axillary Lymph Node Metastases in Patients with T1 Breast Cancer," *Cancer*, 1994, 350-353, vol. 73, No. 2.

Chott, A., et al., "Tyrosine Kinases Expressed in Vivo by Human Prostate Cancer Bone Marrow Metastases and Loss of the Type 1 Insulin-Like Growth Factor Receptor," *American Journal of Pathology*, 1999, 1271-1279, vol. 155, No. 4.

Cohen, B. D., et al., "Combination Therapy Enhances the Inhibition of Tumor Growth with the Fully Human Anti-Type 1 Insulin-Like Growth Factor Receptor Monoclonal Antibody CP-751, 871," *Clinical Cancer Research*, 2005, 2063-2073, vol. 11, No. 5.

Cristofanilli, M., et al., "Circulating Tumor Cells: A Novel Prognostic Factor for Newly Diagnosed Metastatic Breast Cancer", *Journal of Clinical Oncology*, 2005, 1420-1430; Errata 4808, vol. 23, No. 1.

Cristofanilli, M., et al., "Circulating Tumor Cells, Disease Progression, and Survival in Metastatic Breast Cancer," *The New England Journal of Medicine*, 2004, 781-791, vol. 351, No. 8.

De Bono, J. S., et al., "Potential Applications for Circulating Tumor Cells Expressing the Insulin-Like Growth Factor-I Receptor", *Clinical Cancer Research*, 2007, 3611-3616, vol. 13, No. 12.

Feezor, R. J., et al., "Significance of Micrometastases in Colorectal Cancer," *Annals of Surgical Oncology*, 2002, 944-953, vol. 9, No. 10.

Fehm, T., et al., Cytogenetic Evidence That Circulating Epithelial Cells in Patients with Carcinoma are Malignant, *Clinical Cancer Research*, 2002, 2073-2084, vol. 8.

Flaig, T. W., et al., "Conference Report and Review: Current Status of Biomarkers Potentially Associated With Prostate Cancer Outcomes", *The Journal of Urology*, 2007, 1229-1237, vol. 177, No. 4.

Flatmark, K., et al., "Immunomagnetic Detection of Micrometastatic Cells in Bone Marrow of Colorectal Cancer Patients", *Clinical Cancer Research*, 2002, 444-449, vol. 8.

Foekens, J. A., et al., "Prognostic Value of Receptors for Insulin-Like Growth Factor 1, Somatostatin, and Epidermal Growth Factor in Human Breast Cancer", *Cancer Research*, 1989, 7002-7009, vol. 49.

Ghossein, R. A., et al., "Review: Polymerase Chain Reaction Detection of Micrometastases and Circulating Tumor cells: Application to Melanoma, Prostate, and Thyroid Carcinomas", *Diagnostic Molecular Pathology*, 1999, 165-175, vol. 8, No. 4.

Glaves, D., "Correlation Between Circulating Cancer Cells and Incidence of Metastases", *British Journal of Cancer*, 1983, 665-673, vol. 48.

Guo, Y., et al., "Characterization of Insulin-Like Growth Factor I Receptors in Human Colon Cancer", *Gastroenterology*, 1992, 1101-1108, vol. 102.

Hayes, D. F., et al., "Monitoring Expression of HER-2 on Circulating Epithelial Cells in Patients With Advanced Breast Cancer", *International Journal of Oncology*, 2002, 1111-1117, vol. 21.

Hellawell, G., et al., "Expression of the Type I Insulin-Like Growth Factor Receptor Is Up-Regulated in Primary Prostate Cancer and Commonly Persists in Metastatic Disease", *Cancer Research*, 2002, 2942-2950, vol. 62.

Kagan, M., et al., "A Sample Preparation and Analysis System for Identification of Circulating Tumor Cells", *Journal of Clinical Ligand Assay*, 2002, 104-110, vol. 25, No. 1.

Kaiser, U., et al., "Expression of Insulin-Like Growth Factor Receptors I and II in Normal Human Lung and in Lung Cancer", Journal of Cancer Research Clinical Oncology, 1993, 665-668, vol. 119.

Larson, C. J., et al., "Apoptosis of Circulating Tumor Cells in Prostate Cancer Patients", *Cytometry*, 2004, 46-53, vol. 62A.

Levsky, J. M., et al., "Single-Cell Gene Expression Profiling", *Science*, 2002, 836-840.

Macaulay, V. M., et al., "Autocrine Function for Insulin-like Growth Factor I in Human Small Cell Lung Cancer Cell Lines and Fresh Tumor Cells", *Cancer Research*, 1990, 2511-2517, vol. 50.

Martin, D. B., et al., "From Genomics to Proteomics: Techniques and Applications in Cancer Research", *Trends in Cell Biology*, 2001, S60-S65, vol. 11, No. 11.

Matsunami, K., et al., "Detection of Bone Marrow Micrometastasis in Gastric Cancer Patients by Immunomagnetic Separation", *Annals of Surgical Onocology*, 2003, 171-175, vol. 10, No. 2.

Meng, S., et al., "Circulating Tumor Cells in Patients with Breast Cancer Dormancy", *Clinical Cancer Research*, 2004, 8152-8162, vol. 10, No. 24.

Moody, T. W., et al., "Growth Factor and Peptide Receptors in Small Cell Lung Cancer", *Life Sciences*, 1993, 1161-1173, vol. 52.

Moreno, J.G., et al., "Circulating Tumor Cells Predict Survival in Patients with Metastatic Prostate Cancer", *Urology*, 2005, 713-718, vol. 65.

Pantel, K., et al., "Detection and Clinical Importance of Micrometastatic Disease", *Journal of the National Cancer Institute*, 1999, 1113-1124, vol. 91, No. 13.

Petrylak, D. P., "Evaluation of Prostate-Specific Antigen Declines or Surrogacy in Patients Treated on SWOG 99-16", *Journal of the National Cancer Institute*, 2006, 516-521, vol. 98, No. 8.

Racila, E., et al., "Detection and Characterization of Carcinoma Cells in the Blood", *Proceedings of the National Academy of Science*, 1998, 4589-4594, vol. 95.

Digiovanni, J., et al., "Deregulated Expression of Insulin-Like Growth Factor 1 in Prostate Epithelium Leads to Neoplasia in Transgenic Mice", *Proceedings of the National Academy of Science*, 2000, 3455-3460, vol. 97, No. 7.

Pollak, M. N., et al., "Presence of Somatomedin Receptors on Primary Human Breast and Colon Carcinomas", *Cancer Letters*, 1987, 223-230, vol. 38.

Remacle-Bonnet, M., et al., "Expression of Type I, but not Type II Insulin-Like Growth Factor Receptor on Both Undifferentiated and Differentiated HT29 Human Colon Carcinoma Cell Line", *Journal of Clinical Endocrinology and Metabolism*, 1992, 609-616, vol. 75, No. 2.

Rao, C., et al., "Automated System to Enumerate Circulating Tumor Cells in Blood", *Proceedings of the AACR*, 2004, vol. 45.

Sandberg-Nordqvist, A., et al., "Characterization of Insulin-Like Growth Factor 1 in Human Primary Brain Tumors," *Cancer Research*, 1993, 2475-2478, vol. 53.

Terstappen, L., et al., "Peripheral Blood Tumor Cell Load Reflects the Clinical Activity of the Disease in Patients with Carcinoma of the Breast," *International Journal of Oncology*, 2000, 573-578, vol. 17.

Therasse, P., et al., "New Guidelines to Evaluate the Response to Treatment in Solid Tumors", *Journal of the National Cancer Institute*, 2000, 205-216, vol. 92, No. 3.

Wu, J., et al., "In vivo Effects of the Human Type I Insulin-Like Growth Factor Receptor Antibody A12 on Androgen-Dependent and Androgen-Independent Xenograft Human Prostate Tumors", *Clinical Cancer Research*, 2005, 3065-3074, vol. 11, No. 8.

International Search Report for PCT/IB2007/001483.

\* cited by examiner

CIRCULATING TUMOR CELL ASSAY

This application is the National Stage of International Application No. PCT/IB2007/001483, filed May 29, 2007, which claims the benefit of U.S. Provisional Application No. 60/810,811, filed Jun. 2, 2006, all of which are incorporated herein by reference in their entirety.

BACKGROUND OF THE INVENTION

The present invention relates to the fields of oncology and diagnostic testing, and more particularly to methods for cancer screening and for predicting and monitoring chemotherapy treatment responses, cancer recurrence or the like.

Insulin-like growth factor (IGF-1) is a 7.5 kD polypeptide that circulates in plasma in high concentrations and is detectable in most tissues. IGF-1, which is structurally similar to insulin, stimulates cell differentiation and cell proliferation, and is required by most mammalian cell types for sustained proliferation. These cell types include, among others, human diploid fibroblasts, epithelial cells, smooth muscle cells, T lymphocytes, neural cells, myeloid cells, chondrocytes, osteoblasts, and bone marrow stem cells.

The first step in the transduction pathway leading to IGF-1-stimulated cellular proliferation or differentiation is binding of IGF-1 or IGF-2 (or insulin at supraphysiological concentrations) to the IGF-1 receptor (IGF-1R). The IGF-1R belongs to the family of tyrosine kinase growth factor receptors (Ullrich et al., *Cell* 61: 203-212, 1990), and is structurally similar to the insulin receptor (Ullrich et al., *EMBO J.* 5: 2503-2512, 1986).

Epidemiological studies suggest that high end normal levels of IGF-1 increase the risk of cancers such as lung, breast, prostate and colorectal, compared to individuals with IGF-1 levels at the low end of normal. Further, there is considerable evidence for a role for IGF-1 and/or IGF-1R in the maintenance of tumor cells in vitro and in vivo. IGF-1R levels are elevated in tumors of lung (Kaiser et al., *J. Cancer Res. Clin. Oncol.* 119: 665-668, 1993; Moody et al., *Life Sciences* 52: 1161-1173, 1993; Macauley et al., *Cancer Res.,* 50: 2511-2517, 1990), breast (Pollak et al., *Cancer Lett.* 38: 223-230, 1987; Foekens et al., *Cancer Res.* 49: 7002-7009, 1989; Arteaqa et al., *J. Clin. Invest.* 84: 1418-1423, 1989), prostate and colon (Remaole-Bennet et al., *J. Clin. Endocrinol. Metab.* 75: 609-616, 1992; Guo et al., *Gastroenterol.* 102: 1101-1108, 1992). Deregulated expression of IGF-1 in prostate epithelium leads to neoplasia in transgenic mice (DiGiovanni et al., *Proc. Nat'l. Acad. Sci. USA* 97: 3455-3460, 2000). In addition, IGF-1 appears to be an autocrine stimulator of human gliomas (Sandberg-Nordqvist et al., *Cancer Res.* 53 (11): 2475-78, 1993), while IGF-1 has been shown to stimulate the growth of fibrosarcomas that overexpress IGF-1R (Butler et al., *Cancer Res.* 58: 3021-3027, 1998). For a review of the role IGF-1/IGF-1R interaction plays in the growth of a variety of human tumors, see Macaulay, *Br. J. Cancer,* 65: 311-20, 1992.

Using antisense expression vectors or antisense oligonucleotides to the IGF-1R RNA, it has been shown that interference with IGF-1R leads to inhibition of IGF-1-mediated cell growth (see, e.g., Wraight et al., *Nat. Biotech.* 18: 521-526, 2000). Growth can also be inhibited using peptide analogues of IGF-1 (Pietrzkowski et al., *Cell Growth & Diff.* 3: 199-205, 1992; Pietrzkowski et al., *Mol. Cell. Biol.* 12: 3883-3889, 1992), or a vector expressing an antisense RNA to the IGF-1 RNA (Trojan et al., *Science* 259: 94-97, 1992). In addition, antibodies to IGF-1R (Arteaga et al., *Breast Canc. Res. Treatm.* 22: 101-106, 1992; and Kalebic et al., *Cancer Res.* 54: 5531-34, 1994), and dominant negative mutants of IGF-1R (Prager et al., *Proc. Nat'l Acad. Sci. USA* 91: 2181-85, 1994; Li et al., *J. Biol. Chem.* 269: 32558-2564, 1994; Jiang et al., *Oncogene* 18: 6071-6077, 1999), an reverse the transformed phenotype, inhibit tumorigenesis, and induce loss of the metastatic phenotype.

IGF-1 is also important in the regulation of apoptosis. Apoptosis, which is programmed cell death, is involved in a wide variety of developmental processes, including immune and nervous system maturation. In addition to its role in development, apoptosis also has been implicated as an important cellular safeguard against tumorigenesis (Williams, *Cell* 65: 1097-1098, 1991; Lane, *Nature* 362: 786-787, 1993). Suppression of the apoptotic program may contribute to the development and progression of malignancies.

IGF-1 protects from apoptosis by cytokine withdrawal in IL-3-dependent hematopoietic cells (Rodriguez-Tarduchy, G. et al., *J. Immunol.* 149: 535-540, 1992), and from serum withdrawal in Rat-1/mycER cells (Harrington, E. et al., *EMBO J.* 13:3286-3295, 1994). The demonstration that c-myc driven fibroblasts are dependent on IGF-1 for their survival suggests that there is an important role for the IGF-1 receptor in the maintenance of tumor cells by specifically inhibiting apoptosis, a role distinct from the proliferative effects of IGF-1 or IGF-1R.

The protective effects of IGF-1 on apoptosis are dependent upon having IGF-1R present on cells to interact with IGF-1 (Resnicoff et al., *Cancer Res.* 55: 3739-41, 1995). Support for an anti-apoptotic function of IGF-1R in the maintenance of tumor cells was also provided by a study using antisense oligonucleotides to the IGF-1R that identified a quantitative relationship between IGF-1R levels, the extent of apoptosis and the tumorigenic potential of a rat syngeneic tumor (Rescinoff et al., *Cancer Res.* 55: 3739-3741, 1995). It has been found that overexpressed IGF-1R protects tumor cells in vitro from etoposide-induced apoptosis (Sell et al., *Cancer Res.* 55: 303-06, 1995) and, even more dramatically, that a decrease in IGF-1R levels below wild type levels caused massive apoptosis of tumor cells in vivo (Resnicoff et al., *Cancer Res.* 55: 2463-69, 1995).

Some studies suggest that expression levels of IGF-1R correlate with clinical outcome. In tumor models, IGF-1R modulates cell proliferation, survival and metastasis and induces resistance to targeted therapies. Inhibition of IGF-1R significantly increases the activity of cytotoxic agents (Cohen, B. e al., *Clin. Cancer Res.* 11(5): 2063-73). Inhibition of IGF-1R signaling thus appears to be a promising strategy for the development of novel cancer therapies.

Malignant tumors of epithelial tissues are the most common form of cancer and are responsible for the majority of cancer-related deaths. Because of progress in the surgical treatment of these tumors, mortality is linked increasingly to early metastasis and recurrence, which is often occult at the time of primary diagnosis (Racila et al., *Proc. Nat'l Acad. Sci. USA* 95:4589-94, 1998; Pantel et al., *J. Nat'l Cancer Inst* 91(13): 1113-24, 1999). For example, the remote anatomical location of some organs makes it unlikely that tumors in those organs will be detected before they have invaded neighboring structures and grown to larger than 1 cm. Even with respect to breast cancers, 12-37% of small tumors of breast cancer (<1 cm) detected by mammography already have metastasized at diagnosis (Chadha M. et al., *Cancer* 73(2): 350-3, 1994.

Circulating tumor cells ("CTCs") are cells of epithelial origin that are present in the circulation of patients with different solid malignancies. They are derived from clones of the primary tumor and are malignant. (See Fehm et al., *Clin. Cancer Res.* 8: 2073-84, 2002.) Evidence has accumulated in the literature showing that CTCs can be considered an independent diagnostic for cancer progression of carcinomas (Beitsch & Clifford, *Am. J. Surg.* 180(6): 446-49, 2000 (breast); Feezor et al., *Ann. Oncol. Surg.* 9(10): 944-53, 2002 (colorectal); Ghossein et al., *Diagn. Mol. Pathol.* 8(4): 165-75, 1999 (melanoma, prostate, thyroid); Glaves, *Br. J. Cancer* 48: 665-73, 1983 (lung); Matsunami et al., *Ann. Surg. Oncol.* 10(2): 171-5, 2003 (gastric); Racila et al., 1998; Pantel et al., 1999).

Detection and enumeration of circulating tumor cells is important for patient care for a number of reasons. They may be detectable before the primary tumor, thus allowing early stage diagnosis. They decrease in response to therapy, so the ability to enumerate CTCs allow one to monitor the effectiveness of a give therapeutic regimen. They can be used as a tool to monitor for recurrence in patients with no measurable disease in the adjuvant setting. For example, CTC were found to be present in 36% of breast cancer patients 8-22 years after mastectomy, apparently from micrometastases (deposits of single tumor cells or very small clusters of neoplastic cells). Meng et al., *Clin. Can. Res.* 1024): 8152-62, 2004.

In addition, CTCs may be used to predict progression-free survival (PFS) and overall survival (OS), as the presence/number of circulating tumor cells in patients with metastatic carcinoma has been shown to be correlated with both PFS and OS. See e.g., Cristofanilli et al., *J. Clin. Oncol.* 23(1): 1420-1430, 2005; Cristofanilli et al., *N. Engi. J. Med.* 351(8): 781-791, 2004.

However, there remains a need for rapid and reliable assays that are more sensitive than mere detection of CTCs.

SUMMARY OF THE INVENTION

The present invention is directed to a method for predicting efficacy of IGF-1R antagonist therapy in a patient, comprising the steps of: a) obtaining a biological specimen from the patient; b) preparing a sample wherein the biological specimen is mixed with a ligand that reacts specifically with tumor cells, to the substantial exclusion of other sample components; c) contacting the sample with at least one reagent that specifically binds epithelial cells; d) contacting the sample with an agent having binding affinity for insulin-like growth factor receptors (IGF-1R) on cells; and e) analyzing the sample to determine the presence of tumor cells expressing IGF-1R, the presence of tumor cells expressing IGF-1R in the sample being predictive of efficacy of IGF-1R antagonist therapy in the patient.

The present invention is also directed to a method for monitoring efficacy of an IGF-1R antagonist therapy in a patient, comprising the steps of: a) obtaining a first biological specimen from the patient; b) preparing a first sample wherein the first biological specimen is mixed with a ligand that reacts specifically with tumor cells, to the substantial exclusion of other sample components; c) contacting the first sample with at least one reagent that specifically binds epithelial cells; d) contacting the first sample with an agent having binding affinity for insulin-like growth factor receptors (IGF-1R) on cells; e) analyzing the first sample to determine the presence and number of tumor cells expressing IGF-1R; f) administering to the patient an IGF-1R antagonist therapy; g) after administering the IGF-1R antagonist therapy, obtaining a second biological specimen from the patient; h) preparing a second sample from the second biological specimen, wherein the second biological specimen is mixed with the ligand that reacts specifically with tumor cells, and performing steps c)-e) on the second sample; and i) comparing the number of tumor cells expressing IGF-1R in the first sample to the number of tumor cells expressing IGF-1R in the second sample, with a lower number in the second sample being indicative of effectiveness of the IGF-1R antagonist therapy in the patient.

In a preferred embodiment, the IGF-1R antagonist therapy is an anti-IGF-1R antibody.

The present invention is further directed to a kit for screening a patient sample for the presence of circulating tumor cells expressing IGF-1R, comprising: a) coated magnetic nanoparticles comprising a magnetic core material, a protein base coating material, and an antibody that binds specifically to a characteristic determinant of the tumor cells, the antibody being coupled, directly or indirectly, to said base coating material; b) a cell specific dye for excluding sample components other than the tumor cells from analysis; and c) at least one detectably labeled agent having binding affinity for IGF-1R.

With the foregoing and other objects, advantages and features of the invention that will become hereinafter apparent, the nature of the invention may be more clearly understood by reference to the following detailed description of the invention, the figures, and to the appended claims.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

Each year in the United States, more than 1 million new cases of cancer are diagnosed; approximately one out of every five deaths in this country is caused by cancer or complications associated with its treatment. Considerable efforts are continually directed at improving treatment and diagnosis of this disease. Most cancer patients are not killed by their primary tumor; rather they succumb to metastases: multiple widespread tumor colonies established by malignant cells that detach themselves from the original tumor and travel through the body, often to distant sites. Unfortunately, metastatic colonies are frequently more difficult to detect and eliminate than the primary tumor and it is often impossible to treat all of them successfully. The ability of malignant cells to metastasize remains one of the major obstacles to the treatment of cancer and may be accelerated by the IGF-1 receptor. See, e.g., Bahr et al., Growth Factors 23:1-14, 2005.

Based on the complexity of cancer and cancer metastasis and the frustration in treating cancer patients over the years, many attempts have been made to develop diagnostic tests to guide treatment and monitor the effects of such treatment on metastasis or relapse. Such tests presumably could also be used for cancer screening, replacing relatively crude tests such as mammography for breast tumors or digital rectal exams for prostate cancers.

In view of the knowledge of the relationship of IGF-1 and IGF-1R to certain cancers, studies were undertaken to evaluate the effect of anti-IGF-1R antibodies on the number of circulating tumor cells and their IGF-1R expression, as well as clinical efficacy of the antibodies. An assay to detect and enumerate circulating tumor cells expressing IGF-1R (IGF-1R-positive CTCs) has now been developed that is useful in the diagnosis and treatment of cancer, and superior to prior art methods involving CTCs. The assay may contribute to a better understanding of the biological functions of the IGF-1 receptor. For example, while it has been postulated that elevated IGF-1R levels are needed to trigger the tumor cell invasive/metastatic phenotype, the relationship between levels of IGF-1R expression and metastatic potential has not yet been completely elucidated. It has now been found that patients with high IGF-1R-positive CTC counts appeared to have more aggressive tumors as evidenced by rapid disease progression. A potential relationship between increased IGF-1R expression and metastatic potential could thus be the basis for the detection of IGF-1R-positive CTCs as a predictor of poor outcome and/or therapeutic intervention.

Initially, the CTC-IGF-1R assay methods of the present invention are useful for the early detection of a tumor, or to confirm a diagnosis. They also may be used for assessing prognosis.

The methods of the present invention are also useful for treatment planning. It has been found that patients with IGF-1R-positive circulating tumor cells prior to treatment are more likely to respond to IGF-1R antagonist therapy that those who do not. By screening patients for IGF-1R-positive antibodies prior to the initiation of any treatment, it is possible to pre-select a population most likely to respond to IGF-1R antagonist therapy and plan a treatment regimen accordingly. Potential uses of the CTC-IGF-1R assays as biomarkers of anti-IGF-1R antibodies could include identification of an optimal biological dose, dose and treatment regimen selection and determination of treatment duration.

It has been found that there is a good correlation between changes in the level of IGF-1R-positive CTCs in the blood with chemotherapy and clinical status. In view of this correlation, it is also possible to assess the patient's response to treatment, or disease progression using the assay methods of the present invention. Measurement of IGF-1 receptors on circulating tumor cells provides a real pharmacodynamic (PD) endpoint. Once treatment has started, measurement of IGF-1R on tumor cells can be used to determine if maximum inhibition of the target has been reached without reaching maximum tolerated dose (MTD). The development of resistance to a given treatment can also be monitored. An additional benefit of the present invention is that drug effect can be determined more frequently by measuring CTC than by traditional means.

Finally, the methods of the present invention may also be used to detect recurrence of a tumor, even in the absence of clinical symptoms.

The methods of the present invention may be used in conjunction with the diagnosis and/or treatment of non-hematological malignancies, including cancers of the breast, prostate, ovaries, lung and colon, particularly non-small cell lung cancer (NSCLC) and hormone-refractory prostate cancer (HRPC).

Screening of patients with multiple tumor types indicates that CTCs and IGF-1R-positive CTCs are frequently detected in HRPC patients. The identification of these cells in HRPC may have prognostic or therapeutic implications. In fact, in a previous study, the presence of CTCs was found to be the most significant parameter predictive of survival in HRPC patients (Moreno et al., *Urology* 65: 713-718, 2005). Multiple studies have established a role for IGF-1R in the development of prostate cancer, and in vitro data suggest that increased IGF-1R expression and/or activity are associated with progression to the hormone refractory phenotype (Hellawell et al., *Cancer Res.*, 62: 2942-2950, 2002; Chott et al., *Am. J. Pathol.* 155: 1271-1279, 1999). In one study described herein, HRPC patients that were considered IGF-1R positive (i.e., at least one IGF-1R-positive CTC detected) had a median level of serum PSA at enrollment higher than those patients with no detectable CTCs. Furthermore, PSA levels and CTC and IGF-1R-positive CTC counts changed in parallel during treatment response or disease progression. It has previously been shown that patients with progressive metastatic HRPC had CTC counts significantly higher than those in the earlier disease group, and a drop in CTC counts one week after initial treatment with docetaxel was reported in two patients (Moreno et al., 2005, supra). Both patients, however, progressed, exhibiting a rise in CTC counts and PSA levels despite additional doses of docetaxel. The studies described herein suggest that only sustained decreases in CTC counts are associated with response to therapy in HRPC. Thus, CTG counts may provide prognostic information independent to that of PSA level. Importantly, preclinical data indicate that changes in PSA in response to anti-IGF-1R treatment reflect changes in prostate tumor growth (Wu et al., *Clin. Cancer Res. II:* 3065-3074, 2005).

It has also been found that the proportion of responders to combined anti-IGF-1R antibody and docetaxel therapy was higher in those patients with detectable IGF-1R-positive CTCs at study entry than in those in which these cells were not detected. Furthermore, late responses, which are not necessarily associated with clinical benefit (see, e.g., Petrylak et al., *J. Nat'l Cancer Inst* 98: 516-521, 2006), were seen in IGF-1R-CTC, negative patients. These data are suggestive of a potential use of IGF-1R CTC enumeration for the identification of HRPC patients that could benefit from anti-IGF-1R therapy.

The methods of the present invention may be used in the planning and/or monitoring of treatment with various chemotherapeutic compounds that inhibit IGF-1R signaling. Particularly preferred are anti-IGF-1R antibodies such as those described in U.S. Pat. No. 7,037,498 and U.S. Patent Application Publication No. 2005/0069539. Other preferred anti-IGF-1R antibodies include F-50035 and MK-0646 (Pierre Fabre/Merck); 19D12 (Schering-Plough); R1507 (Roche/Genmab); EM-164/AVE-1642 (Immunogen/Sanofi-Aventis); IMC-A12 (ImClone Systems); AMG479 (Amgen); as well as antibodies described in International Patent Application No. WO2006/069202; U.S. Patent Application Publication No. 2005/0147612; U.S. Patent Application Publication No. 2005/0084906; U.S. Patent Application Publication No. 2005/0249730; U.S. Patent Application Publication No. 2004/0018191; U.S. Patent Application Publication No. 2005/0136063; U.S. Patent Application Publication No. 2003/0235582; U.S. Patent Application Publication No. 2004/0265307; U.S. Patent Application Publication No.

2004/0228859; U.S. Patent Application Publication No. 2005/0008642; European Patent Application No. 1622942; U.S. Patent Application Publication No. 2003/0165502; and U.S. Patent Publication No. 2005/0048050.

Other classes of molecules suitable for use with the present invention include peptide aptamers that specifically bind to IGF-1R, antisense oligonucleotide IGF-1R modulators; and small molecule IGF-1R inhibitors. Preferred small molecule IGF-1R inhibitors include OSI-906 (OSI Pharmaceuticals); AEW-541 (Novartis); BMS-536924 and BMS-554417 (Bristol-Myers Squibb); INSM-18 (Insmed); AG-1024 (Pfizer); XL228 (Exelixis), picropodophyllin, and those disclosed in International Patent Application Nos. WO2004/043962 and WO2004/054996.

As set forth below in greater detail, the methods of the present invention involve the selective removal of cells having certain antigenic reactive sites from a patient sample. Methods and apparatuses for such selective removal are well known to one of skill in the art. See, e.g., U.S. Pat. Nos. 4,551,435; 4,795,698; 4,925,788; 5,108,933; and 5,200,084; and U.S. Patent Application Publication No. 2004/0157271. In a preferred embodiment, the cells of interest are immunomagnetically isolated from the patient sample using ferrofluids. Ferrofluids contain tiny magnetic particles in a colloidal suspension whose flow can be controlled by magnets or magnetic fields.

In order that this invention may be better understood, the following examples are set forth. These examples are for purposes of illustration only and are not to be construed as limiting the scope of the invention in any manner.

EXAMPLES

In the examples set forth herein, blood samples were taken at multiple geographic locations from human subjects into CELLSAVE Preservative Tubes (Immunicon, Huntingdon Valley, Pa.), evacuated 10 mL blood draw tubes containing a cell preservative to preserve cell morphology and cells surface antigen expression. Samples were maintained at room temperature and processed as described above within 72 hours of blood collection.

Patient response to treatment was assessed radiologically using the Response Evaluation Criteria in Solid Tumors (RECIST) (see Therasse et al., *J. Nat'l Cancer Inst.* 92: 205-216, 2000) or, in HRPC patients, using prostate specific antigen working group (PSAWG) criteria (see Bubley et al., *J. Clin. Oncol.* 17:3461-3467, 1999).

Example 1

Development of IGF-1R Circulating Tumor Cell Assay

Cell Culture and Cell Spiking:

The breast cancer cell line MCF-7, the prostate cell line PC3-9, the bladder cell line T-24 and the hematopoeitic cell line CEM were cultured in flasks containing RPMI-1640 cell culture medium supplemented with 10% FCS and subsequently harvested using trypsin. The cell suspensions were only used when their viability as assessed by trypan blue exclusion exceeded 90%. To determine the actual cell number, a 50 µL aliquot of the cells was permeabilized and fluorescently labeled by adding 200 µl of PBS containing 0.05% saponin and 10 µl anti-cytokeratin monoclonal antibody conjugated to phycoerythrin (PE) at a final concentration of 0.5 µg/ml. After a 15 minute incubation at room temp, 200 µl of buffer and 20 µl of fluorescent beads (Beckman-Coulter, Inc., Miami, Fla.) containing approximately 20,000 total beads were added. Duplicate tubes containing beads only were run on a flow cytometer (FACSCalibur, BD Biosciences, San Jose, Calif.) until 100% of the sample was aspirated. This provided an accurate estimate of the number of beads present in 20 µl. The experimental tubes were then tested in triplicate on the flow cytometer until 10,000 beads were counted in each tube. Using the known number of beads per unit volume, the concentration of cells was determined. For IGF-1R detection spiked cell numbers were estimated to be between 130 and 220 in 7.5 mL of blood.

Isolation and Enumeration of CTCs:

Samples for the isolation of cells from blood were prepared and analyzed using the CELLTRACKS system (Immunicon, Huntingdon Valley, Pa.), which consists of a CELLTRACKS AUTOPREP system, a reagent kit and the CELLSPOTTER Analyzer. The CELLTRACKS AUTOPREP system is an automated sample preparation system for rare cell detection. The reagent kit consists of ferrofluids coated with antibodies to immunomagnetically enrich cells, a cocktail of fluorescently conjugated antibodies (antibodies conjugated to PE and allophycocyanin (APC) to label epithelial cells and leukocytes respectively), a nuclear dye, and buffers to wash, permeabilize and resuspend the cells. For the detection of carcinoma cells, 7.5 mL of blood is mixed with ferrofluids coated with antibodies directed against the tumor-associated antigen EpCAM (epithelial cell adhesion molecule, or epithelial cell surface antigen): After immunomagnetic enrichment, fluorescein isothyocyanate (FITC)-labeled antibodies recognizing cytokeratins 4, 5, 6, 8, 10, 13, 18 and 19, APC-labeled antibodies recognizing leukocyte antigen CD45, PE-labeled antibodies recognizing IGF-1R, and the nucleic acid dye 4',6-diamidino-2-phenylindole (DAPI) were added in conjunction with a permeabilization buffer to fluorescently label the immunomagnetically-labeled cells. After incubation on the system, the magnetic separation was repeated and excess staining reagents were aspirated. In the final processing step, the cells were resuspended in the MAGNEST Cell Presentation Device (Immunicon, Huntingdon Valley, Pa.). This device consists of a chamber and two magnets that orient the immunomagnetically-labeled cells for analysis using a fluorescent microscope.

The MAGNEST was placed on the CELLSPOTTER Analyzer, a four color semi-automated fluorescent microscope. Image frames covering the entire surface of the cartridge for each of the four fluorescent filter cubes were captured. The captured images containing objects that met predetermined criteria were automatically presented in a web-enabled browser from which final selection of cells was made by the operator. The criteria for an object to be defined as a CTC included round to oval morphology, a visible nucleus (DAPI positive), positive staining for cytokeratin, and lack of expression of CD45 (as determined by negative CD45-APC staining). Results of cell enumeration were always expressed as the number of cells per 7.5 mL of blood.

Selection of IGF-1R Antibodies and Detection of EGF-1R on Tumor Cell Lines:

The anti-IGF-1R antibodies 1H7 (PE conjugate; BD Biosciences, San Jose, Calif.) and 33255.111 (R&D Systems, Minneapolis, Minn.) were titrated on cells from the breast cancer cell line MCF-7 cells. Cross blocking experiments demonstrated no inhibition suggesting that these antibodies bind to different and noncompetitive epitopes of the IGF-1R. Cross blocking experiments with CP-751,871 human anti-IGF-1R antibody (Pfizer Inc.; see U.S. Pat. No. 7,037,498) showed that antibody 33255.111 was completely blocked from binding cells by essentially equimolar amounts of CP-751,871. The 1H7 antibody, in contrast, showed no inhibition of binding in the presence of CP-751,871. These data demonstrate that 33255.111 and CP-751,871 bind to either the same or related epitopes. Since the binding of the 1H7 antibody to IGF-1R is not blocked in the presence of CP-751, 871, 1H7 was selected for further evaluation.

Figure 1:
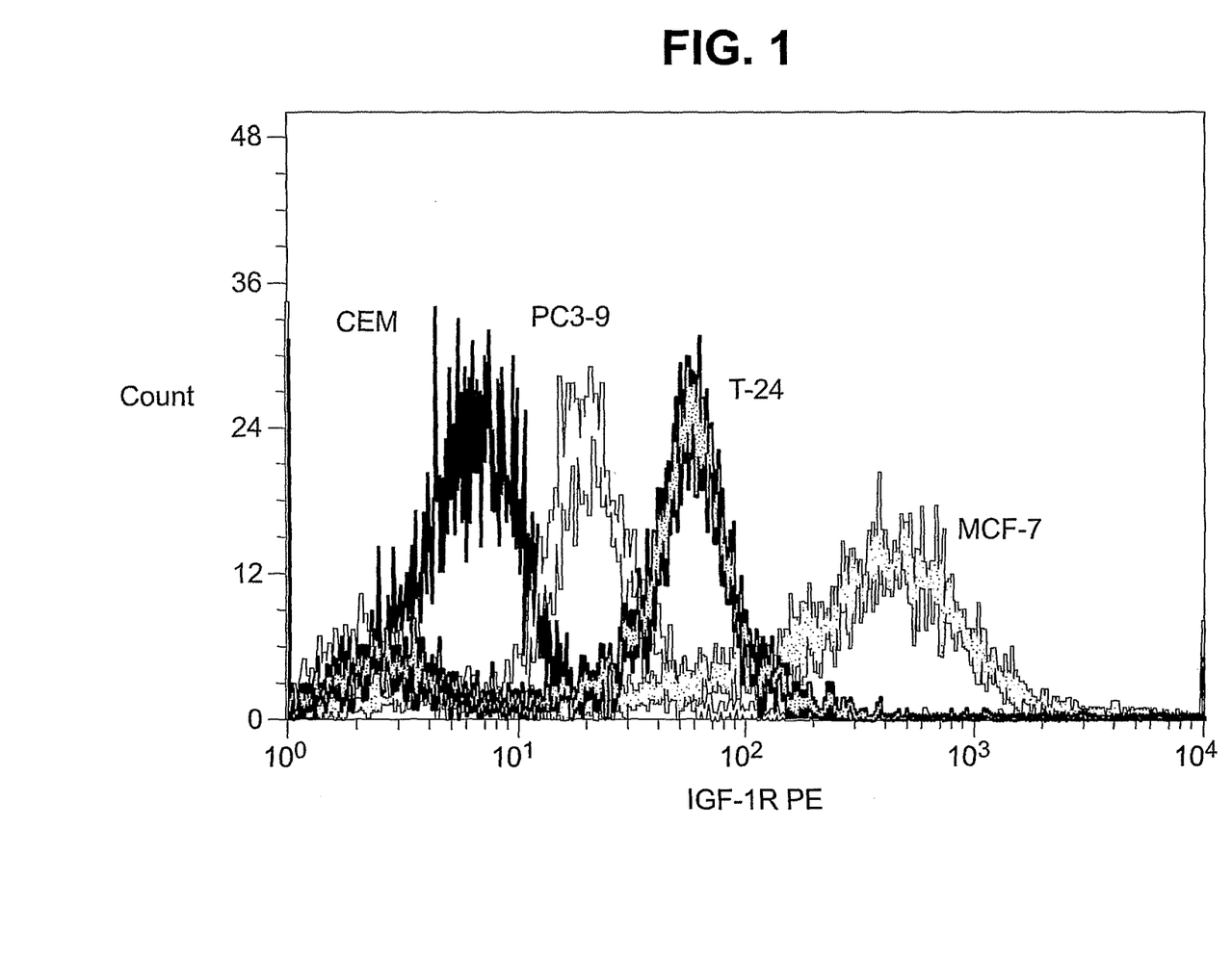
FIG. 1 is an overlay of histograms of the IGF-1R-phycoerythrin staining of various cell lines.

The antigen density on the hematopoeitic cell line CEM, the prostate cancer cell line PC3-9, the bladder cell line T-24 and the MCF-7 breast cancer cell line was assessed by staining with the PE-labeled anti-IGF-1R antibody 1H7 followed by flowcytometric analysis. FIG. 1 shows an overlay of histograms of the IGF-1R-PE staining of the cell lines. Staining of CEM cells was similar to that of the controls and IGF-1R density was thus below the detection limit. IGF-1R-PE staining of the PC3-9 cells could be resolved from the background and T24 and MCF-7 cells clearly had a brighter staining. Estimation of the antigen density was obtained by qualibration of the flow cytometer with beads with a known number of PE molecules. IGF-1R density on the PC3-9 cells was approximately 10,000 IGF-1R antigens, on T-24 cells approximately 50,000 IGF-1R antigens and on MCF-7 cells approximately 1,000,000 IGF-1R antigens.

IGF-1R Assay Characterization:

The standard CTC assay using the CELLTRACKS system uses PE for detection of cytokeratin present on cells of epithelial origin, APC for detection of CD45 present on cells of hematopoeitic origin, and FITC for detection of analyte specific reagents on CTCs defined as cytokeratin-positive, CCD45-negative nucleated cells. The current limitation of detection of the CELLSPOTTER Analyzers for detection of antigens with FITC-labeled antibodies is approximately 100,000 antigens per cell. To increase this sensitivity, the CTC assay was reconfigured to lower the detection limit for IGF-1R detection. Cytokeratin expressed at high densities on epithelial cells was labeled with FITC, which permitted the use of the PE-labeled anti-IGF-1R antibodies. In separate experiments 130 to 200 PC3-9, T-24 or MCF-7 cells were spiked into 7.5 mL of blood and prepared with the newly configured staining reagents. After preparation the samples were scanned on the CELLSPOTTER Analyzer. The analyzer was reconfigured such that cytokeratin FITC-positive, nucleated DAPI-positive events were presented to the user as CTC candidates.

Figure 2:
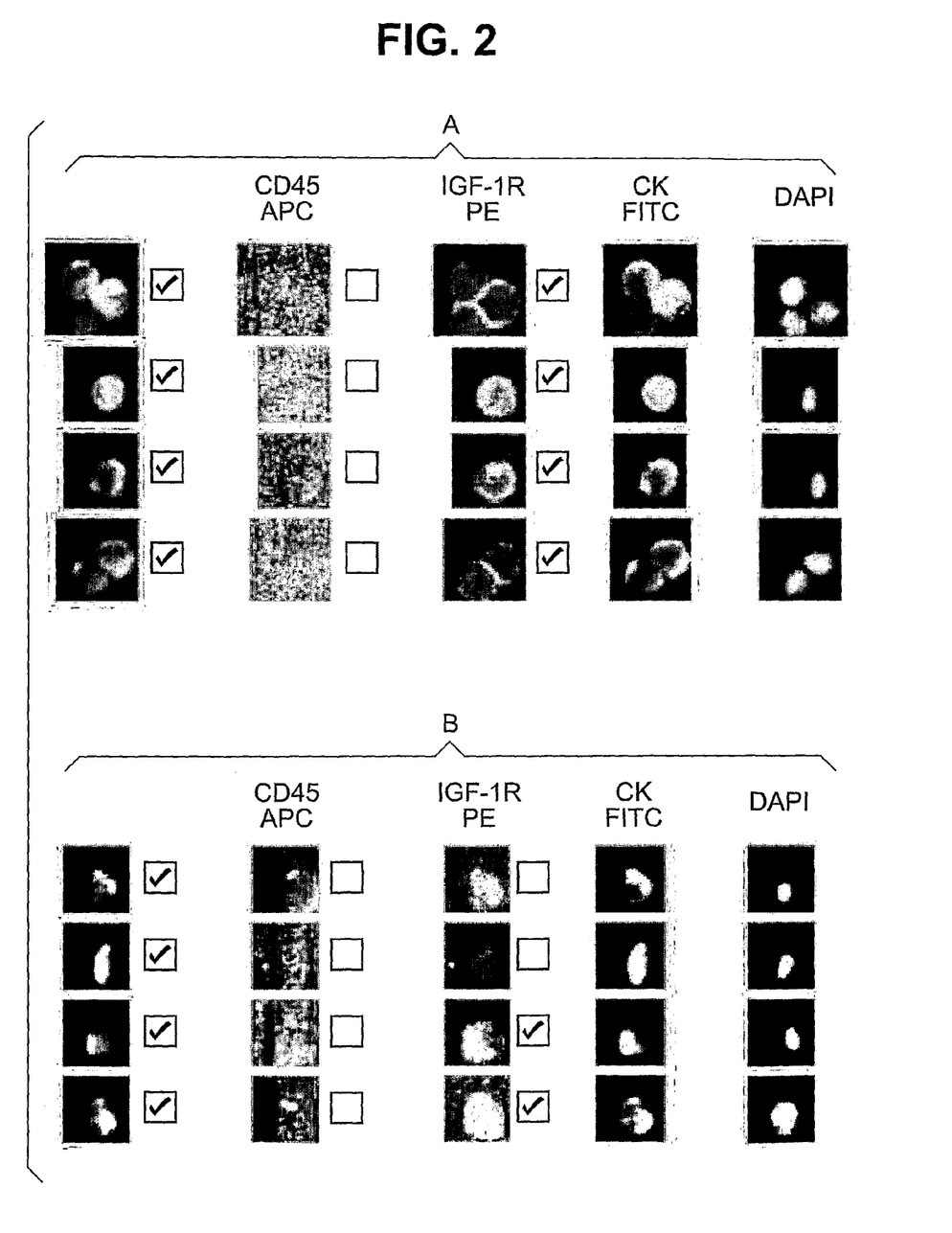
FIG. 2 is a collection of fluorescent microscope images of labeled MCF-7 breast cancer cells (Panel A) and T-24 bladder cells (Panel B).

In Panel A of FIG. 2 a typical example of MCF-7 cells recovered from 7.5 mL of blood is shown. The top row shows a cluster of 3 MCF-7 cells that clearly expressed the IGF-1R receptor, the checkmark next to the composite image indicates that the operator classified the cell as a CTC and the checkmark next to the image showing the IGF-1R staining indicated that the operator classified this CTC as one that expressed IGF-1R. All cells shown in Panel A clearly expressed the IGF-1R receptor. In blood from sixteen healthy individuals spiked with MCF-7 cells 80.6% (SD7.7) of the recovered MCF-7 cells were classified as CTCs that expressed IGF-1R. In Panel B of FIG. 2 a typical example of T-24 cells recovered from 7.5 mL of blood is shown. Expression of IGF-1R of the four T-24 cells was clearly dimmer as compared to the IGF-1R staining of MCF-7 cells and the operator only classified the bottom two cells as CTCs that expressed the IGF-1R receptor. In blood from six healthy individuals spiked with T-24 cells, 13.6% (SD3.9) of the recovered MCF-7 cells were classified as CTCs that expressed IGF-1R. In blood from six healthy individuals spiked with PC3-9 cells, 3.8% (SD6.0) of the recovered MCF-7 cells were classified as CTCs that expressed IGF-1R. These data provided guidance for the IGF-1R antigen density on CTCs of patients with metastatic carcinomas that is needed for it to be detected by this assay.

Figure 3:
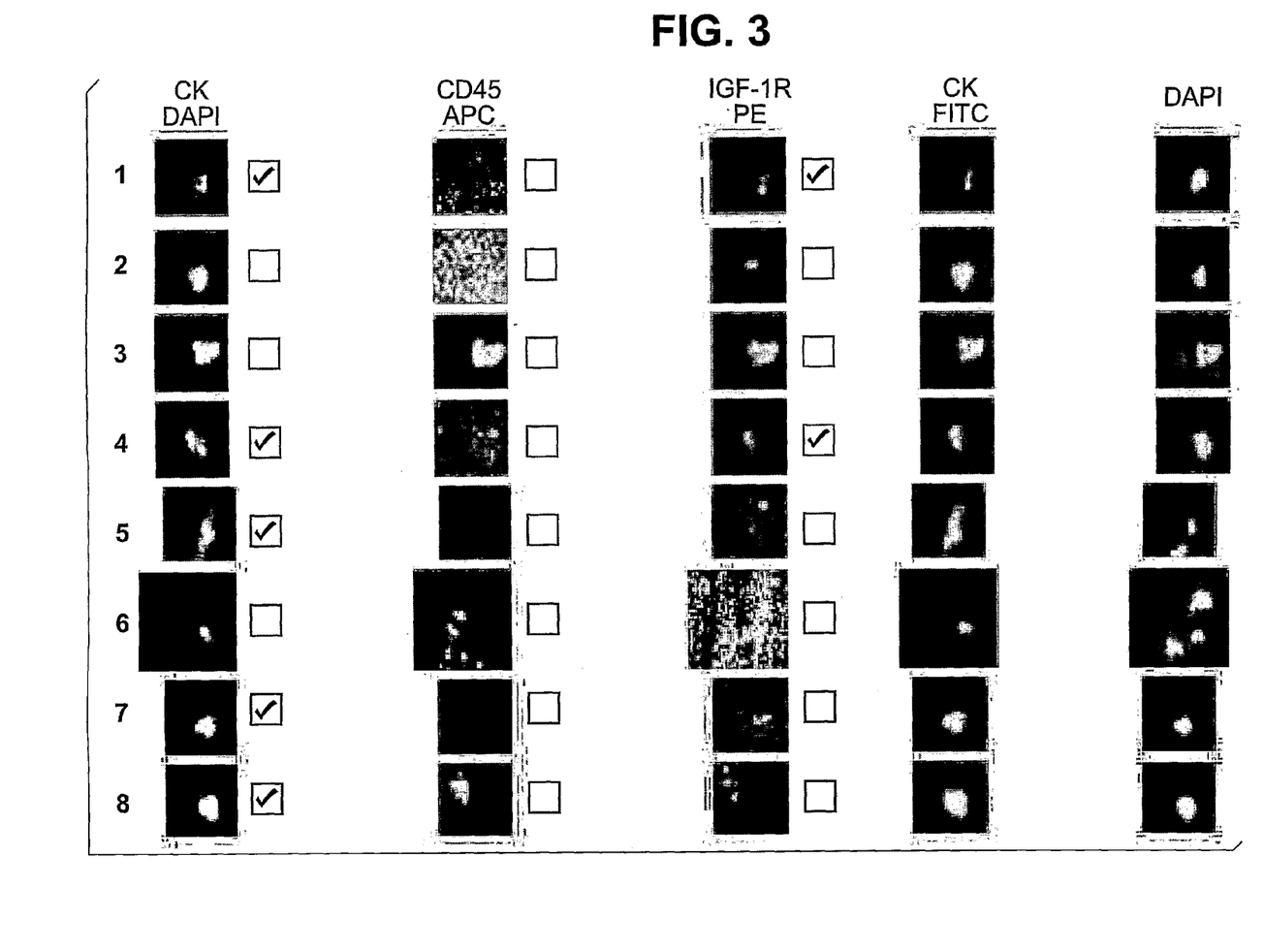
FIG. 3 is a collection of fluorescent microscope images of potential circulating tumor cells.
Figure 4A:
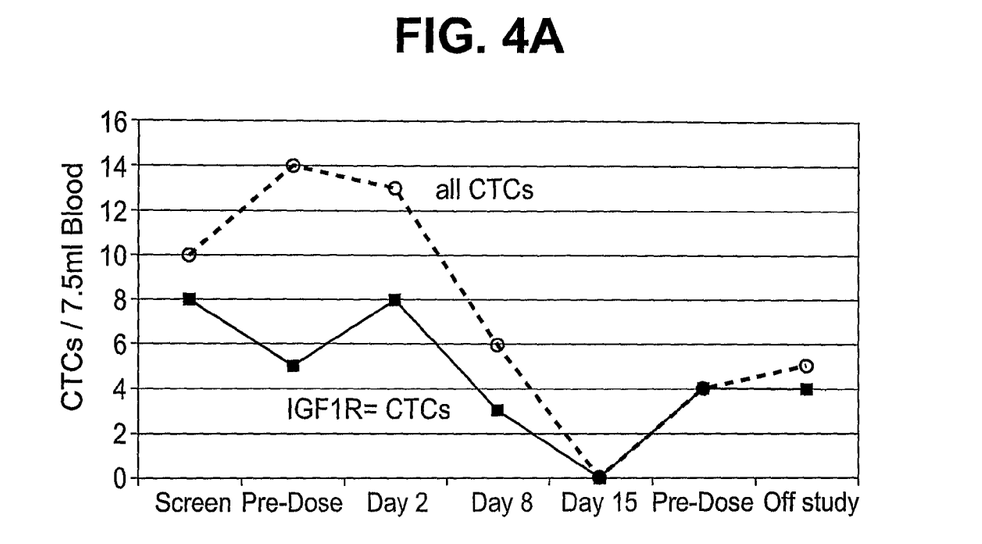
FIG. 4 is a graphic representation of the number of total circulating tumor cells and IGF-1R-positive circulating tumor cells of four patients treated with an anti-IGF-1R antibody.
Figure 4B:
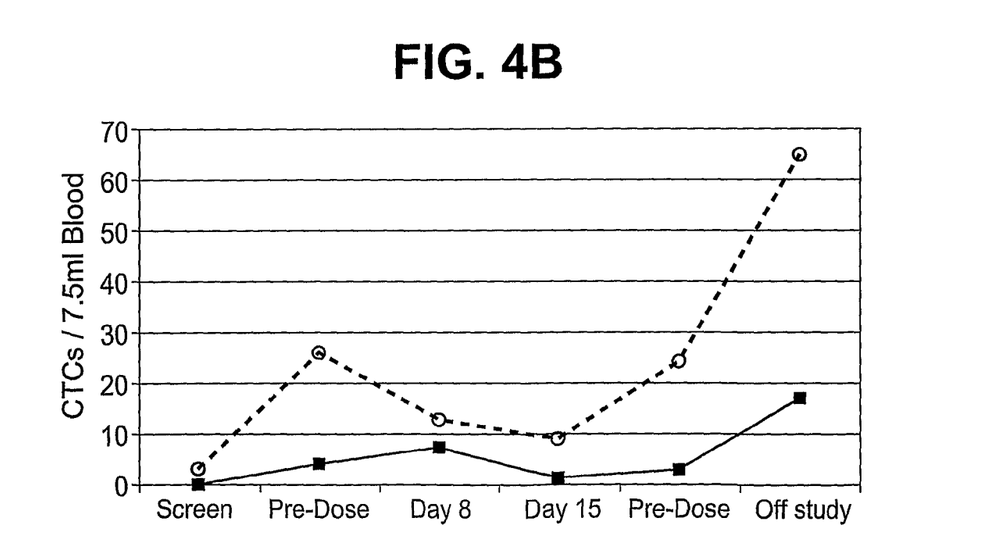
Figure 4C:
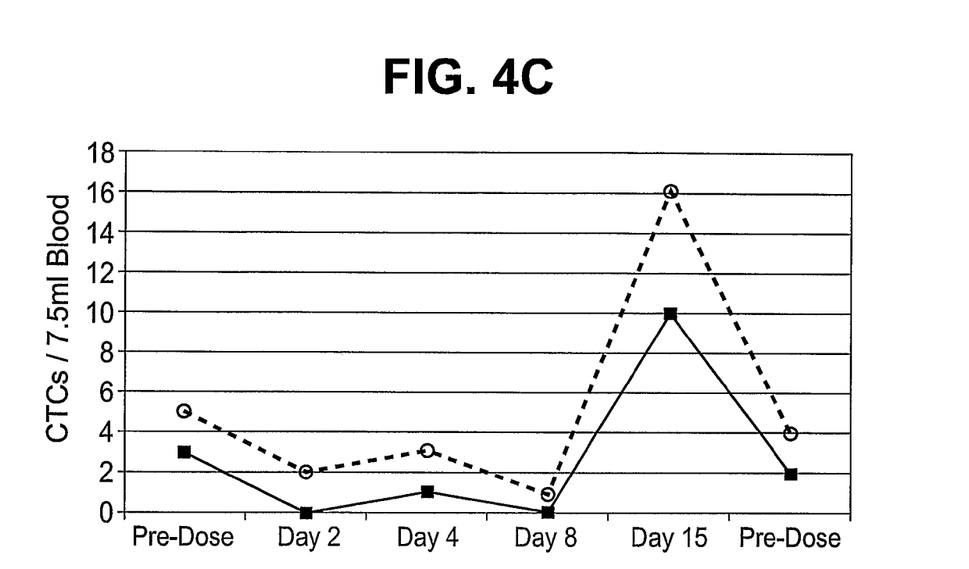
Figure 4D:
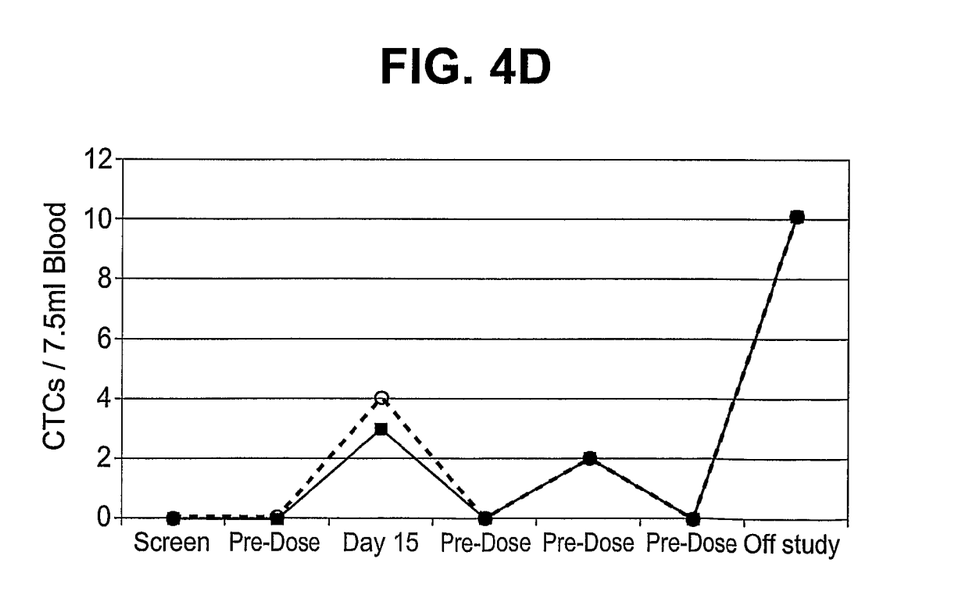
Figure 5A:
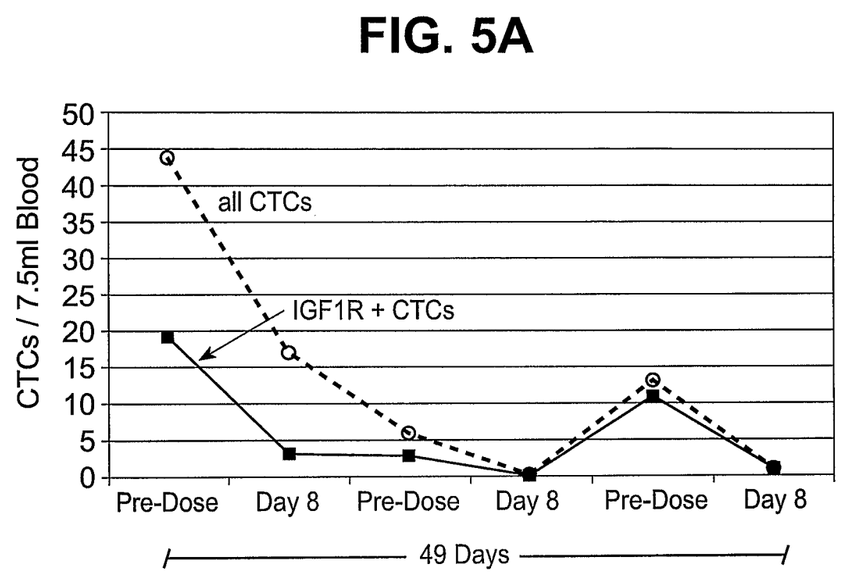
FIG. 5 is a graphic representation of the number of total circulating tumor cells and IGF-1R-positive circulating tumor cells of four patients treated with an anti-IGF-1R antibody in combination with docetaxel.
Figure 5B:
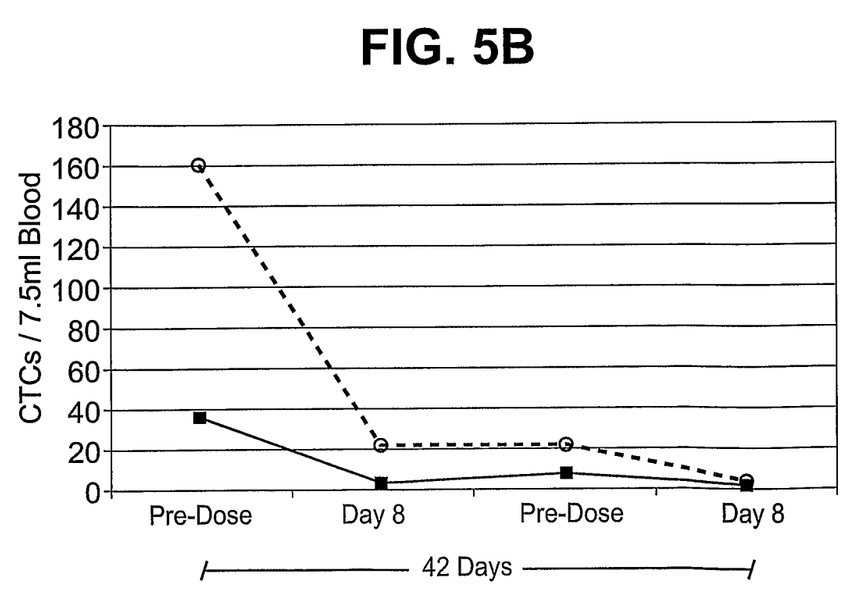
Figure 5C:
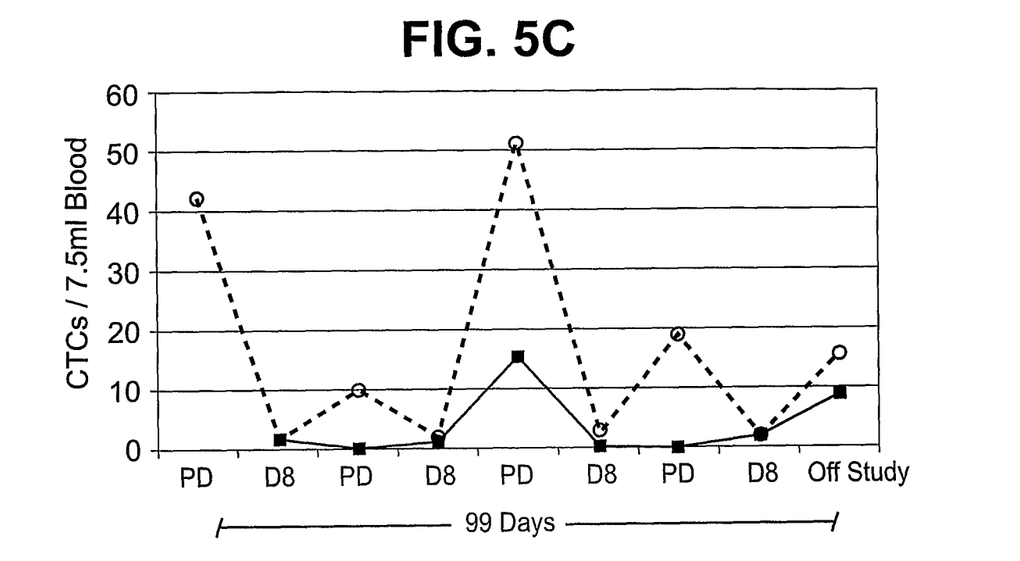
Figure 5D:
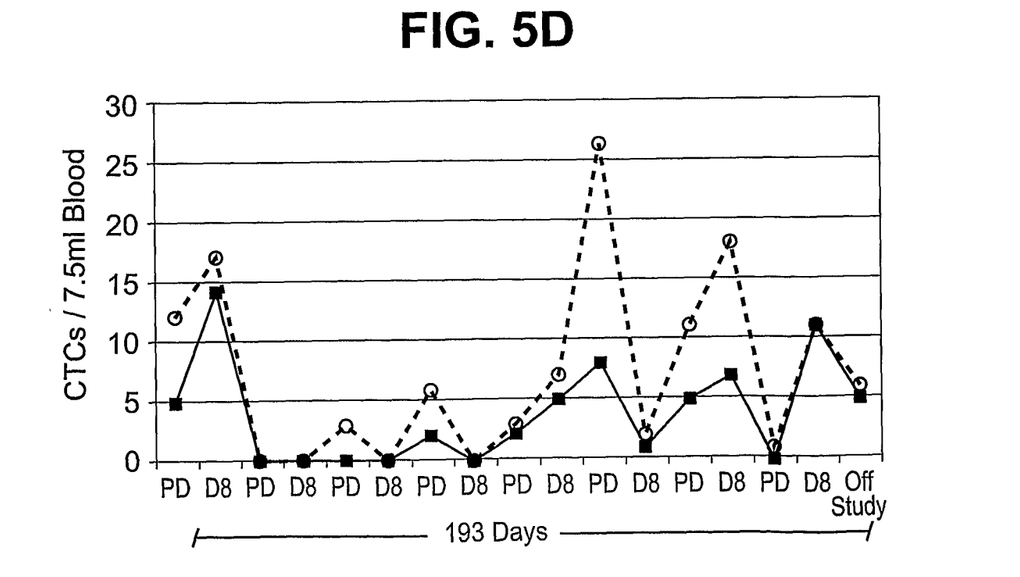
Figure 6A:
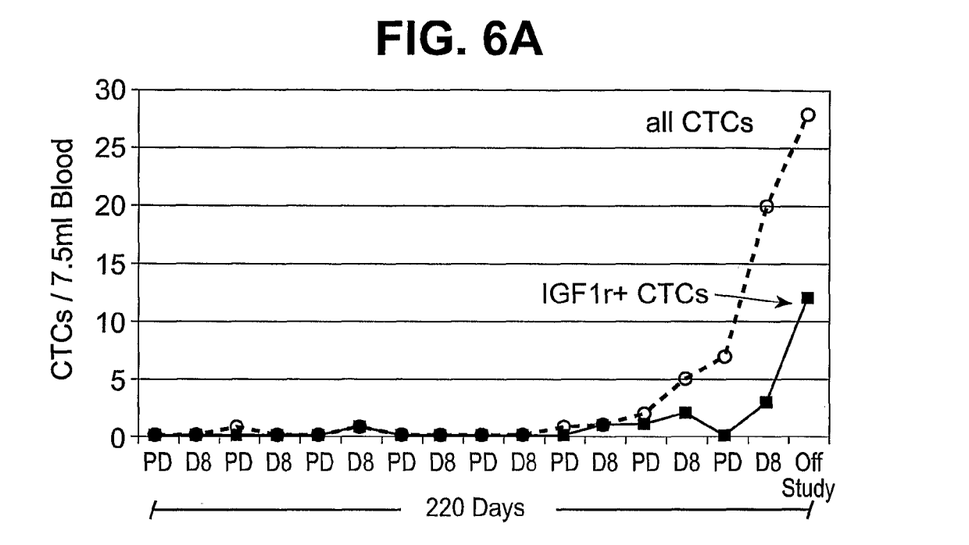
FIG. 6 is a graphic representation of the number of total circulating tumor cells and IGF-1R-positive circulating tumor cells of four patients treated with an anti-IGF-1R antibody in combination with paclitaxel and carboplatin.
Figure 6B:
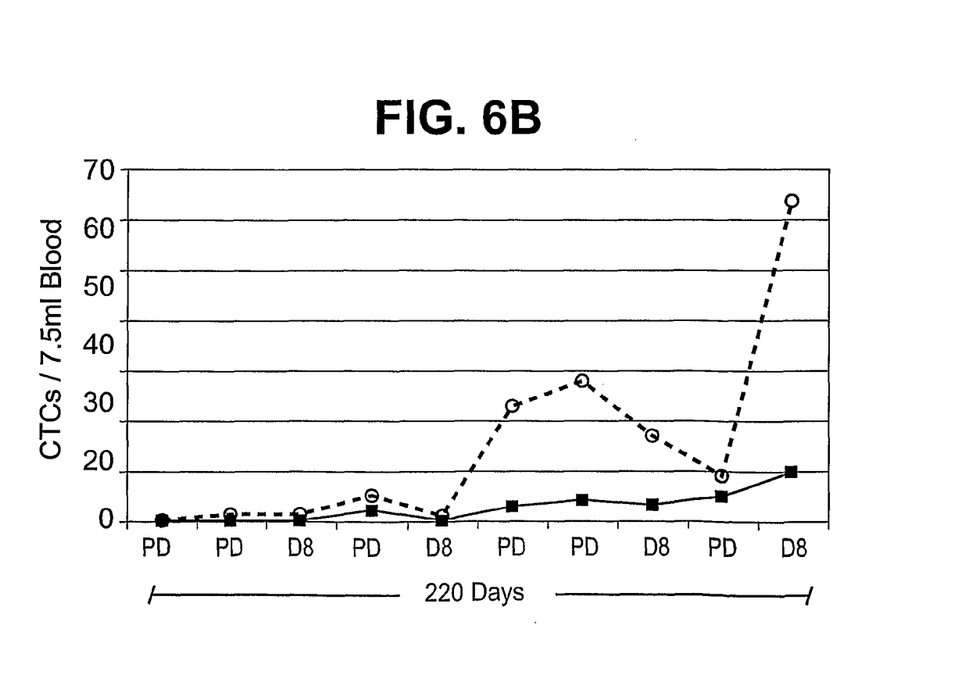
Figure 6C:
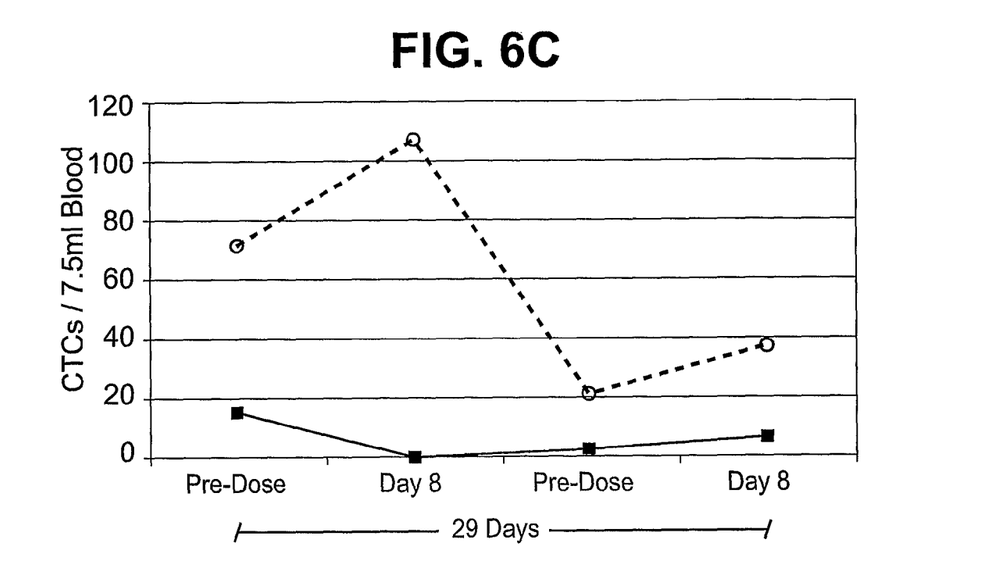
Figure 6D:
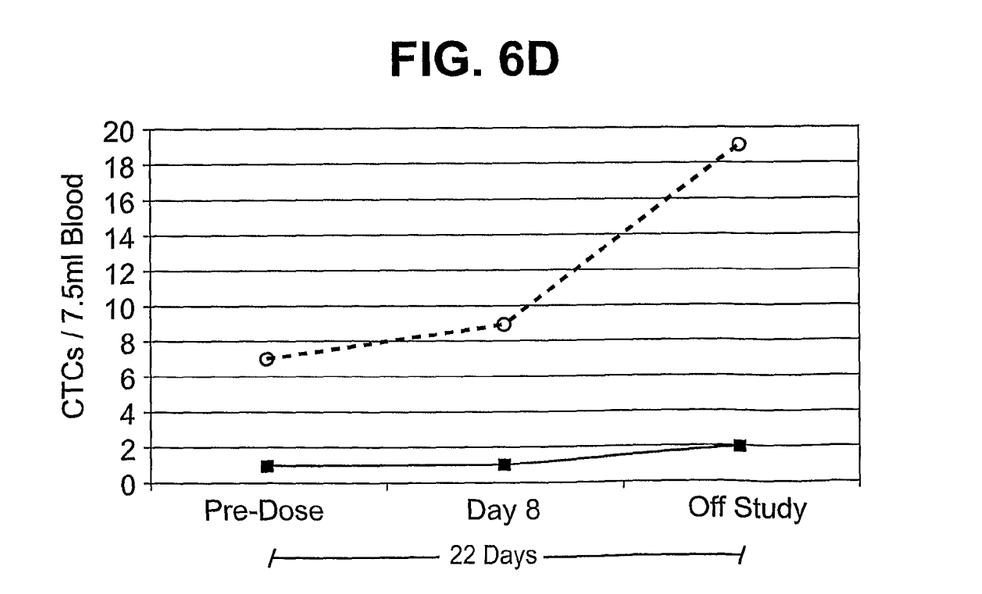

IGF-1R Expression on CTCs in Metastatic Carcinomas:

In 7.5 mL of blood from 139 healthy individuals CTCs were virtually absent (0 CTCs in 135 and 1 CTC in 4). To test whether or not IGF-1R indeed could be detected on CTCs in patients with metastatic carcinomas, blood samples from 50 patients were tested. In 7.5 mL of blood CTCs were detected in 11 of 50 (22%) patients. Among these 50 patients 18 had breast cancer and in 28% CTCs were detected, 13 had colorectal cancer and in 31% CTCs were detected, 3 had prostate cancer and in 33% CTCs were detected, 12 had lung cancer and in 8% CTCs were detected and in none of the 4 patients with ovarian cancer CTCs were detected. Examples of CTCs detected are shown in FIG. 3. Eight CTC candidates are shown in the figure. Events 1, 4, 5, 7 and 8 were classified as CTCs and only CTCs in row 1 and 4 were classified as CTCs that expressed IGF-1R. Note that potential IGF-1R staining can be observed in CTCs in row 5 and 7 but this was not considered sufficient for classification as IGF-1R positive CTCs. Table 1 shows the number of CTCs detected in the 11 patients with CTCs, the number of CTCs that expressed IGF-1R, and the proportion of CTCs that express IGF-1R. In 8 of the 11 (91%) patients CTCs were detected that expressed IGF-1R. The proportion of CTCs that expressed IGF-R, however, varied greatly.

TABLE 1

|  | CTCs | IGF-1R(+) CTCs | % IGF-1R(+) CTCs |
|---|---|---|---|
| Breast | 180 | 47 | 26 |
|  | 25 | 11 | 44 |
|  | 5 | 1 | 20 |
|  | 4 | 1 | 25 |
| Colorectal | 6 | 1 | 17 |
|  | 5 | 0 | 0 |
|  | 4 | 0 | 0 |
|  | 2 | 0 | 0 |
|  | 1 | 1 | 100 |
| Prostate | 16 | 1 | 6 |
| Lung | 2 | 1 | 50 |

Example 2

IGF-R Expression on CTCs in Phase 1 Dose-Finding Study of Anti-IGF-1R Antibody

Study 1 was a dose-finding Phase 1 study designed to define the safety and tolerability of a fully human anti-IGF-1R antibody as described in U.S. Pat. No. 7,037,498 in patients with advanced solid tumors. In this study, the anti-IGF-1R antibody treatment was given every 21 days (21-day cycle) at doses from 3 to 20 mg/kg. In order to evaluate the effect of treatment with anti-IGF-1R antibody on the number of CTCs and CTCs expressing IGF-1R in these patients, blood samples were drawn at screening, on Day 1 pre-dosing and study Day 8 of each 21-day treatment cycle. One additional sample Was taken whenever a patient withdrew from the study due to disease progression. Twenty-six patients provided blood samples for the enumeration of CTCs during the course of the study.

Sixteen of the twenty-six patients (61%) had one or more CTCs at some point during the study (pre-dosing or while on treatment). In three of the sixteen patients with CTCs detected at some point during the study, no IGF-1R-positive CTCs were detected. In two cases only one CTC was detected in 7.5 mL of blood. Levels of CTCs and IGF-1R-positive CTCs were plotted in relation to time and several patterns of response to anti-IGF-1R antibody treatment were observed. Four examples are depicted in FIG. 4. In Panel A, CTC counts from a patient treated with a single dose of 6 mg/kg of anti-IGF-1R antibody is shown. In this patient, the number of CTCs and IGF-1R-positive CTCs decreased at Day 8 of treatment with anti-IGF-1R antibody and were no longer detectable at Day 15 to then reappear before the start of cycle 2. In Panel B, CTC counts from a patient treated with a single dose of 10 mg/kg of anti-IGF-1R antibody is shown. After a slight decrease of CTCs after 8 and 15 days of treatment, the number of CTCs and IGF-1R-positive CTCs increased by the time that the patient was taken off study. This patient presented disease progression by CT scan. In Panel C CTC counts from a patient treated with a single dose of 20 mg/kg of anti-IGF-1R antibody is shown. CTCs and IGF-1R-positive numbers were unaffected except for a spike of CTCs 15 days after administration of the dose. Panel D shows CTC counts from a patient treated with a single dose of 3 mg/kg of anti-IGF-1R antibody in which almost all detected CTCs expressed IGF-1R. An increase of CTCs was noted at the time that the patient was taken off the study. One possible interpretation of these data is that most circulating tumor cells in these patients express IGF-1R and that treatment with anti-IGF-1R antibodies appears to block a survival signal necessary for the preservation of CTCs. Alternatively, the effect of the anti-IGF-1R antibody may take place directly at the tumor mass, inhibiting the migration of CTCs.

Despite variability, a decrease in the number of CTCs and IGF-1R-positive CTCs post-dosing was observed as well as a rebound in the number of circulating cells by the end of the treatment cycle. Increases in the number of CTCs and IGF-1R-positive CTCs were also noted at post-study follow-up visits. These data support a role for CTC and CTC-IGF-1R assays in the monitoring of the biological and clinical response to anti-IGF-1R antibodies.

Example 3

IGF-1R Expression on CTCs in Study of Anti-IGF-1R Antibody in Combination with Docetaxel Study 2 was a phase 1b dose-finding study of a fully human anti-IGF-1R antibody as described in U.S. Pat. No. 7,037,498 in combination with docetaxel (TAXOTERE) in patients with advanced solid tumors. Docetaxel and anti-IGF-1R antibody were administered on Day 1 and Day 22 at doses of 75 mg/m$^2$ and 0.1-10 mg/kg, respectively. Twenty-seven patients provided blood samples for the enumeration of CTCs, including nineteen hormone-refractory prostate cancer (HRPC) patients. CTC samples were collected at each cycle on Day 1 pre-dose and on Day 8.

Nineteen of the twenty-seven patients (70%) had one or more CTCs at some point during the study. In only one of the nineteen patients with CTCs detected at some point of the study, no IGF-1R-positive CTCs were detected. Interestingly, in all 5 CTC assessments of this patient, CTCs were detected and no IGF-1R-positive CTCs were detected, suggesting that the tumor site itself in this patient may not express IGF-1R.

Decreases in the number of CTCs in response to treatment were observed in the majority of patients. Levels of CTCs and IGF-1R-positive CTCs were plotted in relation to time and several patterns of response to anti-IGF-1R antibody treatment were observed. Four examples are depicted in FIG. 5. Panel A depicts the number of CTCs and IGF-1R-positive CTCs in a hormone refractory prostate cancer patient treated with 10 mg/kg of anti-IGF-1R antibody and 75 mg/m$^2$ of docetaxel (21 day-cycle). Following treatment, the total number of CTCs decreased reflecting a response to the combination treatment. PSA values obtained from this patient confirmed a clinical response to treatment. In addition, in this patient, approximately 50% of the CTCs were originally IGF-1R-positive before anti-IGF-1R antibody/docetaxel therapy; the number of IGF-1R-positive CTCs quickly decreased with treatment. Since the biological effect of the anti-IGF-1R antibody is to induce IGF-1R down-regulation, these data support potential roles of the CTC and CTC-IGF-1R assays in the monitoring of both the clinical and biological (biomarker) activity of anti-IGF-1R antibodies. Panel B depicts a patient with a similar decrease in the number of CTCs and IGF-1R positive CTCs. Panel C and D depicts two patients in which the number of CTCs and IGF-1R-positive CTCs decreased after administration of each dose but also rebounded back each time. Both patients were treated with low doses of anti-IGF-1R antibody (0.8 and 3 mg/kg, respectively).

HRPC patients enrolled in Study 2 who had at least one detectable IGF-1R-positive CTC at enrollment had higher PSA levels (n=10, median PSA 475 ng/mL) than those who were IGF-1R-CTC negative (n=8, median PSA 92 ng/mL). No assessment was possible in two patients due to missing samples. Despite the apparent higher tumor burden, patients that were IGF-1R-CTC positive at enrollment responded by PSA criteria in a higher proportion (6 out of 10) and, overall, earlier to the combination of docetaxel and anti-IGF-1R antibody than those who were IGF-1R-CTC negative (2 out of 8), as shown in Table 2:

TABLE 2

| HRPC Patients Responding to Treatment | Baseline PSA (ng/mL) | Baseline CTCs | Baseline IGF-1R (+) CTCs | Treatment Cycle of Initial PSA Response |
|---|---|---|---|---|
| 1006 | 238 | 2 | 1 | 3$^{rd}$ |
| 1008 | 471 | 4 | 1 | 12$^{th}$ |
| 1014 | 9944 | 12 | 5 | 2$^{nd}$ |
| 1019 | 617 | 44 | 19 | 3$^{rd}$ |
| 1022 | 1639 | 6 | 2 | 1$^{st}$ |
| 1025 | 807 | 160 | 37 | 1$^{st}$ |
| 1003 | 13 | 0 | 0 | 6$^{th}$ |
| 1011 | 131 | 0 | 0 | 12$^{th}$ |

Of the eight HRPC patients who had no detectable CTCs at study entry, six did not respond to treatment, and three of them actually experienced an increase in CTC and IGF-1R-positive CTC counts at the time of disease progression. Finally, the one HRPC patient treated with docetaxel and anti-IGF-1R antibodies with detectable CTCs, but no detectable IGF-1R-positive CTCs, did not respond to the combination treatment. The decrease in his CTC count was also short-lived (1 cycle).

In Table 3, a summary of Patient Best Responses for HRPC patients in Study 2 is shown. Two of eight (25%) patients with no detectable IGF-1R-positive CTCs in 7.5 mL before initiation of therapy showed a partial response to therapy whereas six of eleven patients (55%) with ≥1 IGF-1R-positive CTCs in 7.5 mL showed a partial response. These data strongly support the notion that the CTC-IGF-1R assay Could be employed to identify patients that could benefit with anti-IGF-1R antibody therapy, as well as to identify the optimal dose and determine the duration of treatment.

TABLE 3

IGF-1R-Positive Circulating Tumor-Cells
and Patient Best Response in Study 2

| Patient | IGF-1R(+) CTCs at baseline (n) | Best Response |
|---|---|---|
| 1001 | 2 | PD |
| 1005 | 2 | SD |
| 1006 | 1 | PR |
| 1008 | 1 | PR |
| 1012 | 31 | PD |
| 1013 | 4 | PD |
| 1014 | 5 | PR |
| 1019 | 19 | PR |
| 1021 | 4 | PD |
| 1022 | 2 | PR |
| 1025 | 37 | PR |
| | | total = 6 PR/11 patients |
| 1002 | 0 | SD |
| 1003 | 0 | PR |
| 1010 | 0 | PD |
| 1011 | 0 | PR |
| 1015 | 0 | SD |
| 1016 | 0 | PD |
| 1018 | 0 | SD |
| 1020 | 0 | SD |
| | | total = 2 PR/8 patients |

PD = progressive disease; SD = stable disease; PR = partial response

Example 4

IGF-1R Expression on CTCs in Study of Anti-IGF-1R Antibody in Combination with Paclitaxel and Carboplatin Study 3 was a phase 1b study of a fully human anti-IGF-1R antibody as described in U.S. Pat. No. 7,037,498 in combination with paclitaxel (TAXOL) and carboplatin (PARAPLATIN) in patients with advanced solid tumors. The doses of paclitaxel, carboplatin and anti-IGF-1R antibody were 200 mg/m$^2$, AUC of 6, and 0.05-10 mg/kg, respectively. Forty-one patients provided blood samples for the enumeration of CTCs. Blood samples were collected at each Cycle on Day 1 pre-dose and on Day 8.

Twenty-one of the forty-one patients (51%) had one or more CTCs at some point during the study, whereas ten of the forty-one patients (24%) had one or more CTCS before the first dose was administered. Sixteen of the forty-one patients (39%) had one or more IGF-1R-positive CTCs at some point during the study, whereas eight of the forty-one patients (20%) had one or more IGF-R-positive CTCs before the first dose was administered. One HRPC patient enrolled in the study had a large number of CTCs at study entry (71 CTCs and 15 IGF-1R-positive CTCS) that decreased in response to treatment (21 CTCs and 2 IGF-1R CTCs by treatment Day 21).

Levels of CTCs and IGF-1R-positive CTCs were plotted in relation to time and several patterns of response to treatment were observed. Four examples are depicted in FIG. 6. Panel A represents data from a patient that joined the study with a very low number of CTCs. After 6 cycles of treatment with paclitaxel/carboplatin and 0.05 mg/kg of the anti-IGF-1R antibody followed by 2 additional cycles of 3 mg/kg of anti-IGF-1R antibody, the patient no longer responded to therapy. This lack of clinical response was associated with a dramatic increase in the number of CTCs and IGF-1R-positive CTCs. Progression of disease in this patient was confirmed by CT scan. In Panel B data are presented from a patient with a similar pattern of rising CTCs and IGF-1R-positive CTCs during the course of the study. In Panels C and D two patients are illustrated with CTCs before the initiation of therapy. The patients received 1.5 and 6 mg/kg of anti-IGF-1R antibody, respectively. The number of IGF-1R-positive cells appear to decrease (Panel C) or remain low (Panel D) while the patient was on anti-IGF-1R treatment. These data further support a potential role of CTCs and CTCs-IGF-1R assays in the monitoring of the effect and the development of resistance to anti-IGF-1R antibody treatments.

Although certain presently preferred embodiments of the invention have been described herein, it will be readily apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A method for predicting efficacy of IGF-1R antagonist therapy in a patient, comprising the steps of:
    a) preparing a sample wherein a blood sample from the patient is mixed with an antibody to epithelial cell adhesion molecule (EpCAM), so as to obtain a cell population enriched for tumor cells;
    b) contacting the enriched cell population with an anti-cytokeratin antibody labeled with fluorescein isothiocyanate (FITC);
    c) contacting the enriched cell population with a phycoerythrin (PE)-labeled antibody to insulin-like growth factor receptors (IGF-1R); and
    d) determining the presence of cells bound by both the anti-cytokeratin antibody and the anti-IGF-1R antibody;
    wherein the presence of cells bound by both antibodies is predictive of efficacy of IGF-1R antagonist therapy in the patient.

2. A method for monitoring efficacy of an IGF-1R antagonist therapy in a patient, comprising the steps of:
    a) preparing a first sample wherein a first blood sample from the patient is mixed with an antibody to epithelial cell adhesion molecule (EpCAM), so as to obtain a cell population enriched for tumor cells;
    b) contacting the enriched cell population with an anti-cytokeratin antibody labeled with fluorescein isothiocyanate (FITC);
    c) contacting the enriched cell population with a phycoerythrin (PE)-labeled antibody to insulin-like growth factor receptors (IGF-1R);
    d) determining the presence and number of cells bound by both the anti-cytokeratin antibody and the anti-IGF-1R antibody;
    e) preparing a second sample from a second blood sample from the patient, after administration of an IGF-1R antagonist therapy, wherein the second blood sample is mixed with the antibody to EpCAM, and performing steps b)-d) on the second sample; and
    f) comparing the number of cells bound by both the anti-cytokeratin antibody and the anti-IGF-1R antibody in the first sample to the number of cells bound by both antibodies in the second sample;
    wherein a lower number of cells bound by both antibodies in the second sample is indicative of efficacy of the IGF-1R antagonist therapy in the patient.

* * * * *

UNITED STATES PATENT AND TRADEMARK OFFICE
CERTIFICATE OF CORRECTION

| | | |
|---|---|---|
| PATENT NO. | : 8,940,493 B2 | Page 1 of 1 |
| APPLICATION NO. | : 12/303243 | |
| DATED | : January 27, 2015 | |
| INVENTOR(S) | : Gualberto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1014 days.

Signed and Sealed this
Twenty-second Day of March, 2016

Michelle K. Lee
*Director of the United States Patent and Trademark Office*